United States Patent [19]

Kuhla et al.

[11] Patent Number: 4,954,494
[45] Date of Patent: Sep. 4, 1990

[54] PYRIDYL-PYRIDAZINONE AND PYRIDYL-PYRAZOLINONE COMPOUNDS AND THEIR USE IN THE TREATMENT OF CONGESTIVE HEAT FAILURE

[75] Inventors: Donald E. Kuhla, Doylestown; Henry F. Campbell, Lansdale; William L. Studt, Harleysville; William C. Faith, Ambler, all of Pa.

[73] Assignee: Rorer Pharmaceutical Corporation, Fort Washington, Pa.

[21] Appl. No.: 303,879

[22] Filed: Jan. 30, 1989

Related U.S. Application Data

[60] Division of Ser. No. 11,490, Feb. 5, 1987, Pat. No. 4,826,835, which is a continuation-in-part of Ser. No. 790,426, Oct. 23, 1985, Pat. No. 4,783,463.

[51] Int. Cl.$^5$ ............... C07D 401/14; A61K 31/44; A61K 31/495; A61K 31/535
[52] U.S. Cl. ..................... 514/210; 514/222; 514/234; 514/252; 514/318; 514/340; 514/341; 514/227.8; 514/236.2; 514/236.5
[58] Field of Search ............... 514/210, 222, 234, 252, 514/318, 340, 341; 544/60, 131, 364; 546/193, 194, 276, 278

[56] References Cited

U.S. PATENT DOCUMENTS 4,847,251  7/1989  Mertens ............................... 544/238

Primary Examiner—Mark L. Berch
Attorney, Agent, or Firm—James A. Nicholson; Imre (Jim) Balogh

[57] ABSTRACT

This invention relates to pyridyl-pyrazolinone compounds of the formula

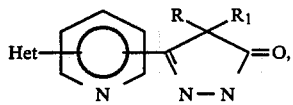

uses of said compounds as cardiotonic agents including methods for increasing cardia contractility and the treatment of congestive heart failure, pharmaceutical compositions including the same and methods for the preparation thereof.

19 Claims, No Drawings

PYRIDYL-PYRIDAZINONE AND PYRIDYL-PYRAZOLINONE COMPOUNDS AND THEIR USE IN THE TREATMENT OF CONGESTIVE HEAT FAILURE

This is a divisional application of application Ser. No. 011,490 U.S. Pat. No. 4,826,835 which is a continuation-in-part of application Ser. No. 790,426 filed Oct. 23, 1985, U.S. Pat. No. 4,783,463.

FIELD OF INVENTION

This invention relates to pyridazinone and pyrazolinone compounds useful as cardiotonic agents for the treatment of congestive heart failure, to their preparation and to pharmaceutical compositions including the same.

REPORTED DEVELOPMENTS

Congestive heart failure is a life threatening condition in which myocardial contractility is depressed such that the heart is unable to adequately pump the blood returning to it. Normal pathologic sequelae include decreased cardiac output, venous pooling, increased venous pressure, edema, increased heart size, increased myocardial wall tension, and eventually cessation of contractility. Digitalis glycosides have long been used to increase myocardial contractility and reverse the detrimental changes seen in congestive heart failure. More recently, dopamine, dobutamine, and amrinone have been used to provide necessary inotropic support for the failing heart.

Other reported inotropic drugs include the substituted pyridazinones disclosed in U.S. Pat. No. 4,353,905, wherein the 6-position of the pyridazinone is substituted by 4-imidazolyl phenyl, and in U.S. Pat. Nos. 4,397,854 and 4,404,203, where the 6-position of the pyridazinone is substituted by various substituted phenyl groups.

The prior art does not disclose pyridazinones substituted in the 6-position by a 1-imidazolyl pyridyl group.

The present invention relates to a class of novel pyridazinone and pyrazolinone compounds which exhibit cardiotonic activity in humans and mammals.

SUMMARY OF INVENTION

This invention relates to the compounds described by the Formula I

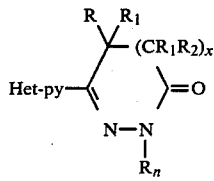

wherein:
Het is imidazol-1-yl or 1,2,4-triazol-1-yl;
py is 2-, 3- or 4-pyridyl
x is 0 or 1;
$R_n$ is hydrogen, alkyl, aralkyl, acyl, carbalkoxy, carbamyl, carbalkoxyalkyl, hydroxyalkyl, alkoxyalkyl or amidino;
$R_1$ and $R_2$ are each independently hydrogen, alkyl or aralkyl;
$R_1$ groups on vicinal carbon atoms may together form a carbon-carbon double bond when $R_n$ is hydrogen and x=1; and
R is hydrogen or —(CH$_2$)$_y$—Y where y is 1-3 and Y is hydrogen, —O—$R_\alpha$, —S—$R_\alpha$ or

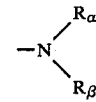

where
$R_\alpha$ is hydrogen, alkyl or acyl and;
$R_\beta$ is hydrogen or alkyl; and
$R_\alpha$ and $R_\beta$ together may form a 3-7 membered ring which may also contain 0-2 additional hetero atoms selected from N, O and S; or a pharmaceutically acceptable salt thereof.

This invention also relates to pharmaceutical compositions for use in increasing cardiac contractility in humans and to the uses of these compounds in the treatment of congestive heart failure in humans and other mammals.

DETAILED DESCRIPTION

Certain of the compounds of Formula I may exist in enolic or tautomeric forms, and all of these forms are considered to be included within the scope of this invention.

The compounds of this invention which have particular usefulness as cardiotonic agents are described by the formulae below.

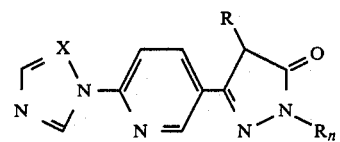

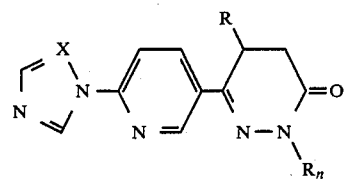

wherein R and $R_n$ are as described above and X is CH or N.

As employed above and throughout the disclosure, the following terms, unless otherwise indicated, shall be understood to have the following meanings.

"Alkyl" means a saturated aliphatic chain, either branched or straight, including up to about 6 carbon atoms.

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"Aralkyl" means an alkyl group substituted by an aryl radical. The preferred aralkyl groups are benzyl or phenethyl.

"Acyl" means an organic radical derived from an organic acid by the removal of its hydroxyl group. Preferred acyl groups are acetyl, propionyl, benzoyl, etc.

"Alkoxy" refers to a loweralkyl—O— group.

The term "halo" means a halogen. Preferred halogens include chloride, bromide, and fluoride.

"2-pyridyl" means a pyridyl ring bonded to the pyridazinone or pyrazolinone ring described in Formula I at the pyridyl carbon ortho to the nitrogen atom.

"3-pyridyl" means a pyridyl ring bonded to the pyridazinone or pyrazolinone ring described in Formula I at the pyridyl carbon meta to the nitrogen atom.

"4-pyridyl" means a pyridyl ring bonded to the pyridazinone or pyrazolinone ring described in Formula I at the pyridyl carbon para to the nitrogen atom.

"Het" means imidazol-1-yl or 1,2,4-triazol-1-yl.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Compounds within the scope of Formula I may be prepared in accordance with one or more of the following reaction sequences.

The 3-pyridyl compounds of Formula I may be prepared from the morpholino cyano intermediate, Formula IV below, according to the reaction sequences shown in Schemes I and II below.

The 2- and 4-pyridyl compounds of Formula I may be prepared using the analogous 2- and 4-pyridyl intermediates.

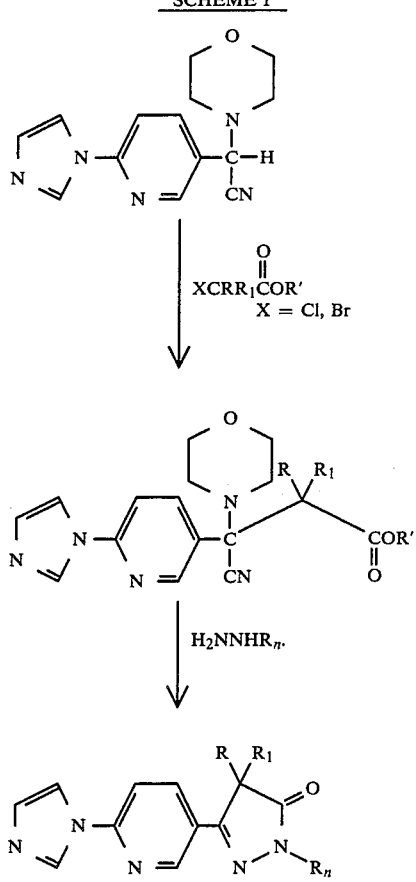

When x in Formula I is 0, the anion of intermediate IV may be alkylated with an alkyl ester of a haloacetic acid and the resulting alkylation product V treated with hydrazine affording the cyclized end product, as shown in Scheme I above.

When x in Formula I is 1, the 6-membered ring may be prepared by reacting the anion of intermediate IV with the ester of an alpha, beta-unsaturated carboxylic acid, thereby forming the 1,4-addition product VI. Reaction of the addition product with a hydrazine forms the cyclized end product, as shown in Scheme II below.

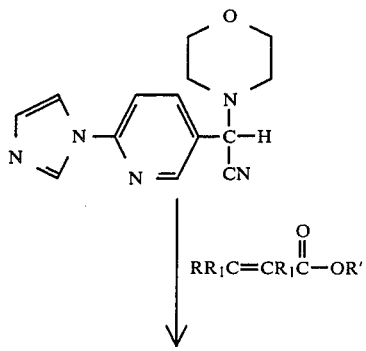

-continued
SCHEME II

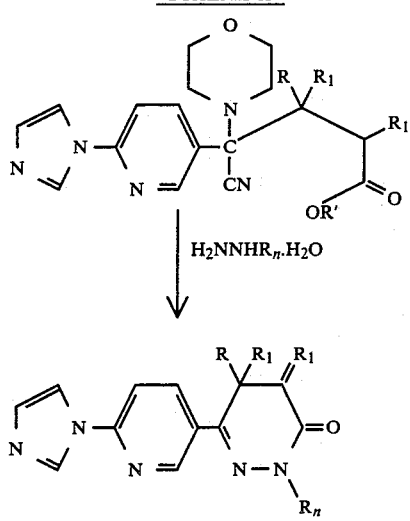

The anion of the intermediate IV may be prepared using a strong base in an aprotic polar solvent such as THF or DMF. The base may be the lithium anion of diisopropyl amine in THF, sodium methoxide in THF or sodium hydride in DMF.

The intermediate IV may be prepared according to the reaction sequence depicted in Scheme III below.

SCHEME III

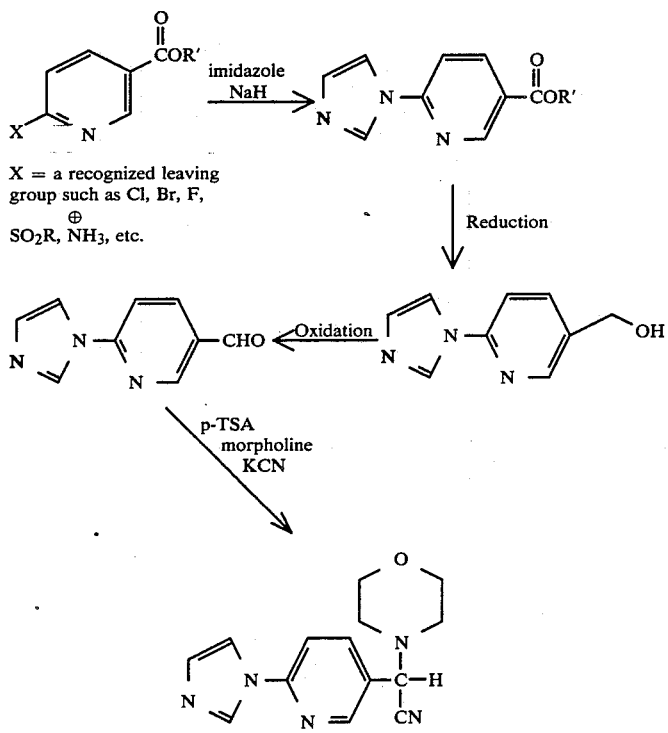

2-Halo nicotinic acid, methyl ester may be treated with imidazole and sodium hydride affording the 2-imidazolyl derivative. The ester functionality is reduced to the alcohol followed by oxidation to the aldehyde. The resulting 2-imidazolyl-5-formyl pyridine is refluxed with p-toluene sulfonic acid and morpholine in THF followed by treatment with potassium cyanide. The cyano morpholino intermediate IV results.

Hydrolysis of the cyano-morpholino propionate or butyrate described as formulae V and VI to the corresponding keto acid VII followed by treatment with an amine of the formula

and formaldehyde results in the corresponding Mannich base. This may then be reacted with a hydrazine to obtain the desired R-substituted product. This is described in Scheme IV.

SCHEME IV

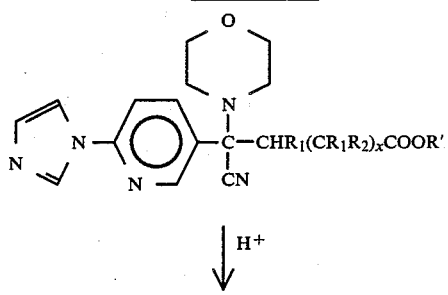

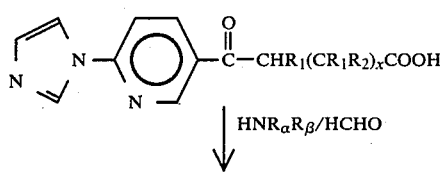

-continued
SCHEME IV

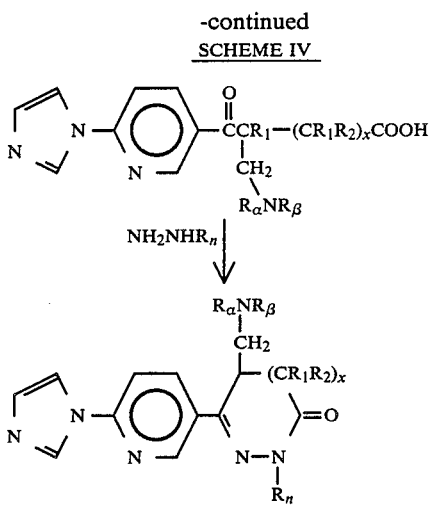

When R is —O—$R_\alpha$ the enolate anion of VII is treated with ethylformate to generate VIII which upon reduction and ring closure with a hydrazine gives the desired product.

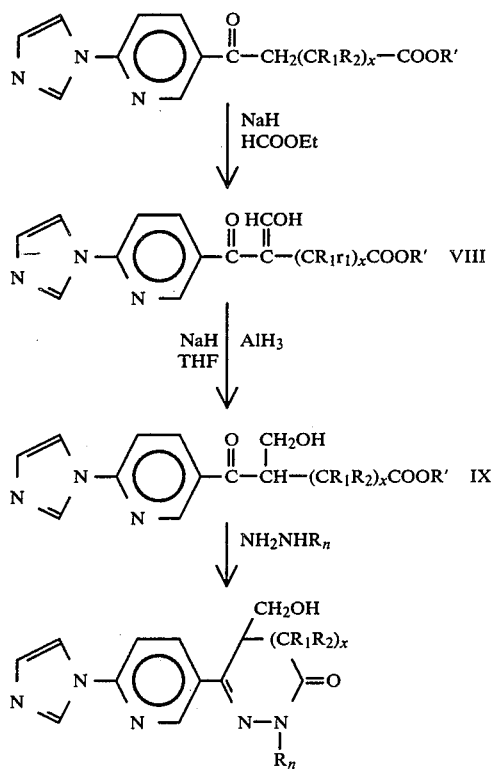

where x is 0 or 1.

The corresponding thio —S—R compound can be prepared by conversion of hydroxymethyl intermediate into the corresponding mesylate, followed by treatment of the latter with a thiol and DBU in benzene. Treatment of the resulting sulfide with a hydrazine produces the thiomethyl derivative of Formula I. This is described below.

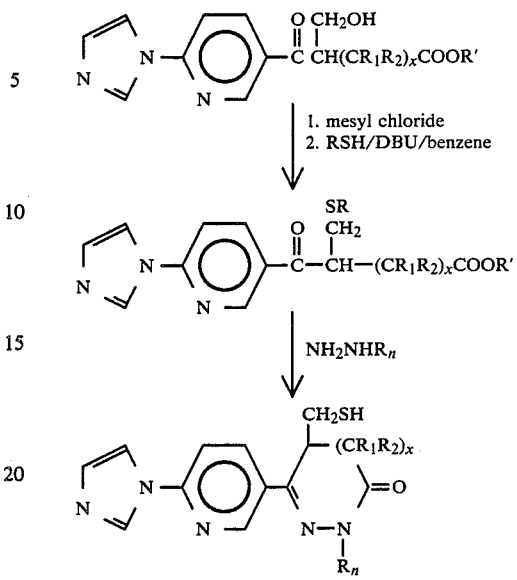

The following are illustrative examples of the preparation of the compounds of the present invention.

EXAMPLE I

PREPARATION OF 4,5-DIHYDRO-6-[6-(1H-IMIDAZOL-1-YL)PYRID-3-YL]-5-METHYL-3-(2H)-PYRIDAZINONE

Step 1. 6-Chloro nicotinic acid, methyl ester

An ethereal solution of $CH_2N_2$ (0.1 mole) is added to a suspension of 6-chloro nicotinic acid (15 g) in $CH_2Cl_2$ until bubbling ceases. The reaction mixture is stirred overnight, evaporated and dried in vacuo affording the desired product as a tan solid used in the next step without further purification.

Step 2. 6-1H-imidazol-1-yl-nicotinic acid, methyl ester

A solution of the methyl ester obtained in Step 1. above (16.29 g) in DMF is added dropwise to a DMF suspension of sodium imidazole [prepared from NaH (4.19 g) and imidazole 6.49 g)] at RT. The reaction mixture is heated to 120° C. for nineteen hours. The cooled reaction mixture is partitioned between water and chloroform, the organic layer separated, washed with water, dried over $Na_2SO_4$, filtered, evaporated, and residual DMF removed under high vacuum yielding the desired product as a tan solid which is recrystalized from methanol (M.P. 183°-184.5° C.) before use in the next step.

Step 3. 2-1H-imidazol-1-yl-5-hydroxymethylpyridine $NaBH_4$ (37.82 g) is added portionwise to a suspension of the imidazolyl ester of Step 2. above (9.98 g) in methanol at about 0.° C. The reaction mixture is heated to reflux for 7½ hours, allowed to cool and stand 15 hours. Water (75 ml) is added, and the quenched reaction mixture evaporated, affording a solid residue which is suspended in water, extracted with chloroform dried over $Na_2SO_4$, filtered and evaporated, recrystallized ($CHCl_3$), affording the desired product as a white solid. M.P.=128.5°-130° C.

Step 4. 2-1H-imidazol-1-yl-5-formylpyridine

MnO$_2$ (18.17 g) is added to a solution of the hydroxy methyl compound of Step 3. above (6.1 g) in CHCl$_3$, and the resulting reaction mixture heated to reflux for 22 hours, allowed to cool, filtered, and the organic layer evaporated affording the desired product as a white solid used in the next step without further purification. M.P.=139.5°–140.5° C.

Step 5. 6-[1H-imidazol-1-yl]-α-cyano-α-N-morpholino-3-picoline

The formyl compound of Step 4 above (5.0 g) is added to a solution of pTSA monohydrate (5.95 g), THF (30.0 ml) and morpholine (5.44 g). The reaction mixture is heated to reflux for 2 hours, cooled and a solution of KCN (2.54 g) in water (4.5 ml) added. Refluxing is continued overnight, after which the reaction mixture is cooled and partitioned between water and chloroform. The chloroform extract is washed with aqueous sodium bisulfite, brine, dried over Na$_2$SO$_4$, filtered and evaporated affording the desired product as a yellow solid used in the next step without further purification.

Step 6. ethyl, 4cyano-4-[6-(1H-imidazol-1-yl)pyrid-3-yl]-3-methyl-4-N-morpholino butyrate A solution of the morpholinyl-cyano methyl compound obtained in Step 5. above (2.0 g) in THF (27 ml) is added dropwise to a solution of lithium diisopropyl amide (0.7 ml of amine) in THF (20 ml) and the reaction mixture is stirred 2.5 hours at −78° C. HMPA (1.34 g) and a solution of LiBr (0.72 g) and ethyl crotonate (0.94 g) in THF (13.0 ml) are added dropwise to the reaction mixture at −78° C. and stirring continued at RT for 40 hours. The mixture is diluted with ether, quenched with saturated NH$_4$Cl (50 ml), extracted with CHCl$_3$, washed with brine, dried over Na$_2$SO$_4$, filtered and evaporated, affording an oil which is dissolved in ethyl acetate and chromatographed (silica gel), eluting with a mixture of ethyl acetate:hexane (85:15). The purified fractions are combined and evaporated to yield the desired product as a yellow solid used in the next step without further purification.

Step 7. 4,5-dihydro-6-[6-(1H-imidazol-1-yl)pyrid-3-yl]-5-methyl-3(2H)-pyridazinone Hydrazine monohydrate (1.85 g) is added to a solution of the product obtained in Step 6. above (2.39 g) in ethanol (20 ml). The reaction mixture is heated to reflux for 94 hours, allowed to stand at RT, filtered and the yellow precipitate washed in ethanol and dried, affording the desired product. M.P.=207°–209.5° C.

EXAMPLE II

PREPARATION OF 4,5-DIHYDRO-6-[6-(1H-IMIDAZOL-1-YL)PYRID-3-YL]-3(2H)-PYRIDAZINONE

Step 1. ethyl, 4-cyano-4-[6-(1H-imidazol-1-yl)pyrid-3-yl]-4-N-morpholino butyrate Potassium hydroxide (0.18 g) is added to a stirring solution of α-cyano-6-(1H-imidazol-1-yl)-α-morpholino-3-picoline (3.0 g) in anhydrous THF (120 ml). The reaction mixture is stirred for 10 minutes and ethyl acrylate (6.03 g) is added to the mixture. Stirring is continued for 2 hours at RT after which a second portion of KOH (0.18 g in 0.5 ml ethanol) and ethyl acrylate 6.03 g) is added. Stirring of the reaction mixture is continued at RT for 19 hours, the mixture is concentrated in vacuo, the oily residue covered with toluene, concentrated in vacuo, the residue dissolved in CHCl$_3$, filtered, and the filtrate concentrated in vacuo yielding an oil. The oil is dissolved in ethyl acetate and chromatographed (silica gel), eluting fractions with ethyl acetate. The pure fractions are combined and concentrated in vacuo, resulting in the desired product as an amber oil.

Step 2. 4,5-dihydro-6-[6-(1H-imidazol-1-yl)pyrid-3-yl]-3-(2H)-pyridazinone

Hydrazine monohydrate (0.41 g) is added to a stirred solution of the product obtained in Step 1. above (2.5 g) in ethanol (50 ml) and the reaction mixture refluxed for 67 hours. A second portion of hydrazine monohydrate (0.41 g) is added to the refluxing reaction mixture and refluxing continued for an additional 4 hours. The cooled mixture is concentrated, and suspended in methanol. Silica gel (8 g; 250–400 mesh) is added and the resulting suspension is concentrated in vacuo. The silica gel residue is stirred in anhydrous ether, concentrated in vacuo, layered onto a silica gel column, and eluted with a mixture of methanol:ethyl acetate (5:95). The slower purified fractions are combined, concentrated in vacuo and the resulting solid dried under high vacuum overnight, affording the desired product as a yellow solid. M.P.=276.5°–278° C., The desired structure is confirmed by IR analysis and by elemental analysis for C$_{12}$H$_{11}$N$_5$O from the following data. Calculated: C (59.74), H (4.6), N (29.03); Found: C (59.31), H (4.48), N (28.63).

EXAMPLE III

PREPARATION OF 3,4-DIHYDRO-5-[6-(1H-IMIDAZOL-1-YL)PYRID-3-YL]-3-PYRAZOLINONE

Step 1. ethyl, 3-cyano-3-[6-(1H-imidazol-1-yl)pyrid-3-yl]-3-N-morpholino propionate A solution of α-cyano-6-[1H-imidazol-1-yl]-α-N-morpholino-3-picoline (1 g) in DMF (3 ml) is added dropwise to a suspension of sodium hydride (0.164 g) in DMF (3 ml) under nitrogen, and stirred at RT for 2 hours. Ethyl bromoacetate (0.62 g) in DMF (3 ml) is added to the mixture, and stirring continued at a lowered temperature (−10° to −15° C.) for about one hour. The reaction mixture is poured into ice, the organic layer extracted with CHCl$_3$, the chloroform extract washed with brine, dried over Na$_2$SO$_4$, filtered, evaporated, and the DMF removed under high vacuum, affording an oil. The oil is chromotographed (silica gel), eluting fractions with a mixture of ethyl acetate:methanol (98:2), and the faster purified fractions combined to afford the desired product which is used in the next step without further purification.

Step 2.
3,4-dihydro-5-[6-(1H-imidazol-1-yl)pyrid-3-yl]-3-pyrazolinone

Hydrazine monohydrate (0.62 g) is added to a solution of ethyl, 3-cyano-3-[6-(1H-imidazol-1-yl)pyrid-3-yl]-3-N-morpholino propionate (0.74 g) in ethanol (15 ml). The reaction mixture is heated to reflux for 22½ hours, allowed to cool and stand for 48 hours. The mixture is filtered and the filtered precipitate dried affording the desired product as a light yellow solid. M.P. >280° C.

EXAMPLE IV

When 5-halo-2-picolinic acid or a 2-haloisonicotinic acid is substituted for 6-chloronicotinic acid in Step 1 of Example I above, then the corresponding 5-(1H-imidazol-1-yl)pyrid-2-yl and 2-(1H-imidazol-1-yl)pyrid-4-yl products are obtained.

EXAMPLE V

When 1-sodium 1,2,4-triazole is substituted for sodium imidazole in Step 2 of Example I above, then the corresponding 6-(1,2,4-triazol-1-yl)pyrid-3-yl; 5-(1,2,4-triazol-1-yl)pyrid-2-yl and 2-(1,2,4-triazol-1-yl)pyrid-4-yl products are obtained.

EXAMPLE VI

Preparation of 4,5-dihydro-5-(N-morpholinomethyl)-6-[6-(1H-imidazol-1-yl)pyrid-3-yl]-3(2H)-pyridazinone

Step 1.
4-[6-(1H-imidazol-1-yl)pyrid-3-yl]-4-oxo-butanoic acid

A solution of ethyl, 4-cyano-4-[6-(1H-imidazol-1-yl)pyrid-3-yl]-4-N-morpholino butyrate (2.34 g, 6.34 mmol) in 14 ml of acetic acid containing 0.9 ml of water is heated to reflux for 1 day. The solvent is removed and the residue is dissolved in CHCl$_3$ and extracted with saturated aqueous NaHCO$_3$ solution. The organic layer is then separated, dried (Na$_2$SO$_4$) and evaporated to give crude ethyl 4-[6-(1H-imidazol-1-yl)pyrid-3-yl]-4-oxo-butanoate. Saponification of the ester in aqueous Na$_2$CO$_3$ at 23° C. generates the desired product used in the next step without further purification.

Step 2.
4-[6-(1H-imidazol-1-yl)pyrid-3-yl]-3-(N-morpholinomethyl)-4-oxo-butanoic acid A mixture of 4-[6-(1H-imidazol-1-yl)pyrid-3-yl]-4-oxo-butanoic acid (1.4 g, 5.73 mmol), morpholine (0.5 g), and 37% aqueous formaldehyde (0.46 g) in 3 ml of H$_2$O is warmed at 70° C. for 3.5 hours, then stirred at 23° C. for 7 days. The aqueous mixture is extracted with CHCl$_3$ and reduced in volume to generate a suspension which is filtered to give the desired product used in the next step without further purification.

Step 3.
4,5-dihydro-5-(N-morpholinomethyl)-6-[6-(1H-imidazol-1-yl)pyrid-3-yl]-3(2H)-pyridazinone A solution of hydrazine monohydrate (0.17 g) and 1.01 g of 4-[6-(1H-imidazol-1-yl)pyrid-3-yl]-3-(N-morpholinomethyl)-4-oxo butanoic acid in ethanol is heated to reflux for 1 day. Upon cooling, a white solid precipitates which is filtered to give the desired product.

EXAMPLE VII

Following the procedures of Exmple VI the amines of Table I below may be used in place of morpholine to obtain the corresponding product.

TABLE I ammonia
ethylamine
diethylamine
methylethylamine
cycolhexylamine
ethyleneimine
trimethyleneimine
piperidine
piperazine
N-methylpiperazine
N-phenylpiperazine
N-benzylpiperazine
N-methylimidazolidine
thiomorpholine
acetamide

EXAMPLE VIII

When hydrazine of the foregoing examples is replaced by the substituted hydrazine of Table I below then the corresponding product is obtained.

TABLE I

| | |
|---|---|
| NH$_2$NHCH$_3$ | NH$_2$NHCONH$_2$ |
| NH$_2$NHCH$_2$CH$_3$ | NH$_2$NHC(=NH)NH$_2$ |
| NH$_2$NHCH$_2$Ph | NH$_2$NHCONHSO$_2$-p-toly |
| NH$_2$NH(CH$_2$)$_2$Ph | NH$_2$NHSO$_2$-p-tolyl |
| NH$_2$NHCOCH$_3$ | |
| NH$_2$NHCH$_2$CH$_2$OH | |
| NH$_2$NHCH$_2$CO$_2$CH$_2$CH$_3$ | |

Tables I through IV below list representative compounds which are within the scope of the present Invention

TABLE I

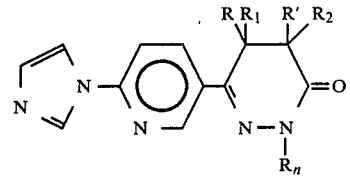

| R | R$_1$ | R$^1$ | R$_2$ | R$_n$ |
|---|---|---|---|---|
| H | H | H | H | H |
| H | | double bond | H | H |
| H | H | H | H | CH$_3$ |
| CH$_3$ | H | H | H | H |
| CH$_3$ | H | H | H | CH$_3$ |
| CH$_3$ | H | H | H | CH$_2$CH$_3$ |
| CH$_3$ | H | H | H | CH$_2$φ |
| CH$_3$ | | double bond | H | H |
| CH$_3$ | H | H | CH$_3$ | H |
| CH$_3$ | H | CH$_3$ | CH$_3$ | H |
| CH$_2$CH$_3$ | H | H | H | H |
| CH$_2$NH$_2$ | H | H | H | H |
| CH$_2$NH$_2$ | H | H | H | CH$_3$ |
| CH$_2$NH$_2$ | H | H | CH$_3$ | H |
| CH$_2$N(CH$_3$)$_2$ | H | H | H | H |
| CH$_2$N(CH$_3$)$_2$ | H | H | H | CH$_3$ |
| CH$_2$N(CH$_3$)$_2$ | H | H | CH$_3$ | H |
| CH$_2$N(CH$_3$)$_2$ | | double bond | H | H |
| CH$_2$N(CH$_2$CH$_3$)$_2$ | H | H | H | H |

TABLE I-continued

Structure: imidazole-N—pyridine—C(R)(R₁)—C(R')(R₂)—C(=O)—N(Rₙ)—N= (pyridazinone ring fused)

| R | R₁ | R¹ | R₂ | Rₙ |
|---|----|----|----|----|
| —CH₂N(piperidinyl) | H | H | H | H |
| —CH₂N(piperidinyl) | H | H | H | CH₃ |
| —CH₂N(piperidinyl) | double bond | | H | H |
| —CH₂N(piperidinyl) | H | H | CH₃ | H |
| —CH₂N(piperidinyl) | H | H | CH₃ | CH₃ |
| —CH₂N(piperidinyl) | double bond | | CH₃ | H |
| —CH₂N(morpholinyl) | H | H | H | H |
| —CH₂N(morpholinyl) | H | H | H | CH₃ |
| —CH₂N(morpholinyl) | H | H | H | CH₂CH₃ |
| —CH₂N(morpholinyl) | H | H | H | CH₂φ |
| —CH₂N(morpholinyl) | H | H | CH₃ | H |
| —CH₂N(morpholinyl) | H | H | CH₃ | CH₃ |
| —CH₂N(morpholinyl) | H | CH₃ | CH₃ | H |
| —CH₂N(morpholinyl) | H | CH₃ | CH₃ | CH₃ |
| —CH₂N(morpholinyl) | double bond | | H | H |
| —CH₂N(N-methylpiperazinyl) | H | H | H | H |
| —CH₂N(N-methylpiperazinyl) | H | H | H | CH₃ |
| —CH₂SH | H | H | H | H |
| —CH₂SCH₃ | H | H | H | H |
| —CH₂SCH₃ | H | H | CH₃ | CH₃ |
| —CH₂OH | H | H | H | H |
| —CH₂OCH₃ | H | H | H | H |
| —CH₂NHC(=O)CH₃ | H | H | H | H |

TABLE II

Structure: imidazole-N—pyridine—C(R)(R₁)—C(=O)—N(Rₙ)—N=

| R | R₁ | Rₙ |
|---|----|----|
| H | H | H |
| CH₃ | H | H |
| H | H | CH₃ |
| CH₂CH₃ | H | CH₃ |
| CH₂N(piperidinyl) | H | H |
| CH₂N(piperidinyl) | H | CH₃ |

TABLE II-continued

| R | R₁ | $R_n$ |
|---|---|---|
| CH₂N⟨O⟩ (morpholinyl) | H | CH₃ |
| CH₂N⟨O⟩ (morpholinyl) | H | CH₂CH₃ |
| CH₂N⟨O⟩ (morpholinyl) | H | CH₂φ |
| CH₃ | CH₃ | CH₃ |

TABLE III

| R | R₁ | R¹ | R₂ | $R_n$ |
|---|---|---|---|---|
| H | H | H | H | H |
| H | double bond | H | H |  |
| CH₃ | H | H | H | H |
| CH₂CH₃ | H | H | H | H |
| CH₃ | H | H | H | CH₃ |
| CH₂N⟨ ⟩ (piperidinyl) | H | H | H | H |
| CH₂N⟨O⟩ (morpholinyl) | H | H | H | H |
| CH₂N⟨O⟩ (morpholinyl) | H | H | H | CH₃ |
| CH₂N⟨O⟩ (morpholinyl) | H | H | CH₃ | CH₃ |

TABLE IV

| R | R₁ | R¹ | R₂ | $R_n$ |
|---|---|---|---|---|
| H | H | H | H | H |
| CH₃ | H | H | H | CH₃ |
| H | H | H | H | CH₃ |
| CH₂N⟨O⟩ (morpholinyl) | H | H | H | CH₃ |

The compounds of Formula I possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Anesthetized Dog Procedure

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular and diastatic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.9–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparnized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular end diastolic pressure, left ventriuclar $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

Guinea Pig Atria Inotropic Screening at Low Calcium Concentrations

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$; 25.00; glucose, 11.66; and $CaCl_2$, 1.25) gassed with a mixture of 95% $O_2$ 5% $CO_2$. Left atria are removed and inserted into warmed 33° C. double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 20 gauge silver wire wound into a tight coil approximately 12–14 mm in diameter. Electrodes are connected to a Grass stimulator via Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets. capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodiumlauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The acqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

We claim:

1. A compound of the formula:

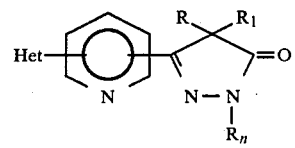

where:

Het is imidazol-1-yl or 1,2,4-triazol-1-yl;

$R_n$ is hydrogen, alkyl, aralkyl, acetyl, propionyl, benzoyl, carbalkoxy, carbamyl, carbalkoxyalkyl, hydroxyalkyl, alkoxyalkyl or amidino;

$R_1$ is hydrogen, alkyl or aralkyl; and

R is hydrogen or $-(CH_2)_y-Y$ where y is 1-3 and Y is hydrogen, $-O-R_{\alpha'}$ $-S-R_\alpha$ or

where $R_\alpha$ is hydrogen, alkyl or acetyl, propionyl, benzoyl and;

$R_\beta$ is hydrogen or alkyl; and $R_\alpha$ and $R_\beta$ together with the nitrogen to which they are attached may form a 3 to about 6 membered ring selected from the group consisting of aziridinyl, azetidinyl, piperidyl, N-methylimidazolidinyl, piperazinyl, substituted piperazinyl where the substituent may be
N-methyl,
N-benzyl or
N-phenyl,
morpholinyl or
thiomorpholinyl; or a pharmaceutically acceptable salt thereof.

2. A compound according to claim 1 where the pyridyl ring is bonded to the pyrazolone ring at the 2-pyridyl carbon position.

3. A compound according to claim 1 where the pyridyl ring is bonded to the pyrazolone ring at the 3-pyridyl carbon position.

4. A compound according to claim 1 where the pyridyl ring is bonded to the pyrazolone ring at the 4-pyridyl carbon position.

5. A compound according to claim 3 where Het is imidazoyl-1-yl.

6. A compound according to claim 3 where Het is 1,2,4-triazol-1-yl.

7. A compound according to claim 5 where R is hydrogen or $-(CH_2)_y-Y$ where y is 1-3 and Y is hydrogen.

8. A compound according to claim 5 where R is

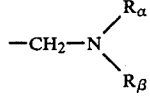

where $R_\alpha$ and $R_\beta$ are hydrogen or alkyl.

9. A compound according to claim 5 where R is

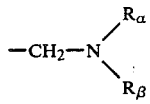

where $R_\alpha$ and $R_\beta$ together with the nitrogen to which they are attached form a 3 to about 6 membered ring selected from the group consisting of aziridinyl, azetidinyl, piperidyl, N-methylimidazolidinyl, piperazinyl, substituted piperazinyl where the substituent may be
N-methyl,
N-benzyl or
N-phenyl,
morpholinyl or
thiomorpholinyl.

10. A pharmaceutical composition for increasing cardiac contractility in a human or other animal requiring such treatment comprising an effective amount of a compound according to claim 1 in admixture with a pharmaceutically acceptable carrier.

11. A method for increasing cardiotonic contractility in a human or other mammal requiring such treatment which comprises administering thereto an effective inotropic amount of a compound of the formula:

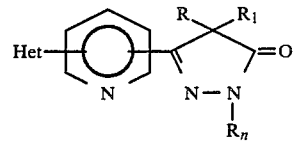

where:

Het is imidazol-1-yl or 1,2,4-triazol-1-yl;

$R_n$ is hydrogen, alkyl, aralkyl, acetyl, propionyl, benzoyl, carbalkoxy, carbamyl, carbalkoxyalkyl, hydroxyalkyl, alkoxyalkyl or amidino;

$R_1$ is hydrogen, alkyl or aralkyl; and

R is hydrogen or $-(CH_2)_y-Y$ where y is 1-3 and Y is hydrogen, $-O-R_{\alpha'}$ $-S-R_\alpha$ or

where $R_\alpha$ is hydrogen, alkyl or acetyl, propionyl, benzoyl and;

$R_\beta$ is hydrogen or alkyl; and $R_\alpha$ and $R_\beta$ together with the nitrogen to which they are attached may form a 3 to about 6 membered ring selected from the group consisting of aziridinyl, azetidinyl, piperidyl, N-methylimidazolidinyl, piperazinyl, substituted piperazinyl where the substituent may be
N-methyl,
N-benzyl or
N-phenyl,
morphonlinyl or
thiomorpholinyl; or a pharmaceutically acceptable salt thereof.

12. A compound according to claim 9 which forms a N-piperazinyl ring.

13. A compound according to claim 9 which forms a N-morpholino ring.

14. A compound according to claim 9 which forms a N-piperdinyl ring.

15. A compound according to claim 13 where $R_n$ and $R_1$ are all hydrogen.

16. A compound according to claim 13 where at least one of $R_n$ and $R_1$ is hydrogen.

17. A compound according to claim 15 which is 2,4-dihydro-4-(N-morpholinomethyl)-5-[6-(1H-imidazol-1-yl)pyrid-3-yl]-3-pyrazolone.

18. A compound according to claim 16 which is 2,4-dihydro-4-(N-morpholinomethyl)-4-[6-(1H-imidazol-1-yl)pyrid-3-yl]-2-methyl-3-pyrazolone.

19. A compound according to claim 7 which is 2,4-dihydro-4,4-dimethyl-5-[6-(1H-imidazol-1-yl)pyrid-3-yl]-3-pyrazolone.

* * * * *

UNITED STATES PATENT AND TRADEMARK OFFICE
CERTIFICATE OF CORRECTION

PATENT NO. : 4,954,494

DATED : September 4, 1990

INVENTOR(S) : D.E. Kuhla, et al

It is certified that error appears in the above-identified patent and that said Letters Patent is hereby corrected as shown below:

On the title page in Item [54] and in Column 1, line 5, the portion reading "HEAT" should read --HEART--.

Signed and Sealed this

Twenty-first Day of January, 1992

Attest:

HARRY F. MANBECK, JR.

*Attesting Officer*      *Commissioner of Patents and Trademarks*